(12) United States Patent
Mita et al.

(10) Patent No.: US 6,858,737 B2
(45) Date of Patent: Feb. 22, 2005

(54) PROCESS FOR PRODUCING 2-CYANOIMINO-1,3-THIAZOLIDINE

(75) Inventors: Shinya Mita, Toyama (JP); Masahiro Murotani, Toyama (JP); Kenichi Ishii, Uozu (JP)

(73) Assignee: Nippon Carbide Kogyo Kabushiki Kaisha, Tokyo (JP)

(*) Notice: Subject to any disclaimer, the term of this patent is extended or adjusted under 35 U.S.C. 154(b) by 10 days.

(21) Appl. No.: 10/470,087

(22) PCT Filed: Oct. 24, 2002

(86) PCT No.: PCT/JP02/11063

§ 371 (c)(1),
(2), (4) Date: Jul. 24, 2003

(87) PCT Pub. No.: WO03/057681

PCT Pub. Date: Jul. 17, 2003

(65) Prior Publication Data

US 2004/0235918 A1 Nov. 25, 2004

(30) Foreign Application Priority Data

Dec. 28, 2001 (JP) ........................ 2001-398702

(51) Int. Cl.[7] ............................ C07D 277/18
(52) U.S. Cl. ........................ 548/198
(58) Field of Search ........................ 548/198

(56) References Cited

U.S. PATENT DOCUMENTS 5,574,165 A   11/1996   Lantzsch
5,591,859 A   1/1997    Thalhammer

FOREIGN PATENT DOCUMENTS

JP    48-91064 A1      11/1973
WO    WO 92/17462 A1   10/1992

OTHER PUBLICATIONS

J. Zmitek et al, "The Synthesis and Reactions of N–Cyano–O–Methylpseudoureas" pp. 721–728 Organic Preparations and Procedures Inc. vol. 23 (6) 1991.

Roberto Toso et al, "New Synthesis of 2–Cyano–1–Methyl–3–{2–{[5–Methyl–1H–Imidazol–4–YL)Methyl ] Thio}Ethyl } Guanidine (Cimetidine)" Gazzetta Chimica Italiana, pp. 345–350,vol. 110, 1980.

R. Neidlein et al, " Reaktionsverhalten von N–Cyanimido–dithiokohlensaureester und 2, 2–Bismethylmercapto–1–cyanacrylnitril" Arch. Pharm. pp. 731–737 vol. 305 (10) (1972).

International Search Report dated Jan. 28, 2003.

*Primary Examiner*—Laura L. Stockton
(74) *Attorney, Agent, or Firm*—Rader, Fishman & Grauer PLLC

(57) ABSTRACT

A method of obtaining a high purity 2-cyanoimino-1,3-thiazolidine, at a high yield, by cyclization reaction of dimethyl N-cyanoiminodithiocarbonate ester with 2-aminoethane thiol or the salt thereof in the presence of an alkali metal hydroxide is disclosed.

7 Claims, No Drawings

PROCESS FOR PRODUCING 2-CYANOIMINO-1,3-THIAZOLIDINE

TECHNICAL FIELD

The present invention relates to an industrial production process for 2-cyanoimino-1,3-thiazolidine useful as an intermediate material for pharmaceuticals and agrochemical materials. More particularly, it relates to a high yield production method of high purity 2-cyanoimino-1,3-thiazolidine from cyclization reaction between dimethyl N-cyanoiminodithiocarbonate ester and 2-aminoethanethiol in the presence of an alkali metal hydroxide.

BACKGROUND ART

Methods for producing 2-cyanoimino-1,3-thiazolidine from the reaction between dimethyl N-cyanoiminodithiocarbonate ester and 2-aminoethanethiol, are those described in Arch. Pharm. (Weiheim, Ger.), 305 (10), P731 (1972), Japanese Unexamined Patent Publication (Kokai) No. 48-91064, Gazz. Chim. Ital., 110 (5–6), P345, and WO92-17462 (1992). This reaction is considered to follow the following formulas:

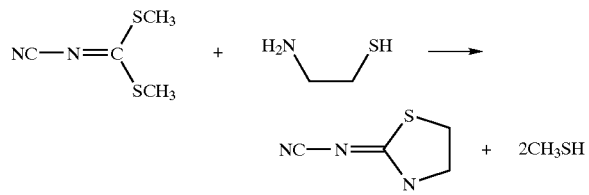

DISCLOSURE OF THE INVENTION

However, in the above proposals in the past, the yield of the 2-cyanoimino-1,3-thiazolidine obtained was low and therefore they were insufficient as industrial production processes.

Accordingly, the objects of the present invention are to solve the above problems in the prior art and to provide an industrial production process capable of producing high purity 2-cyanoimino-1,3-thiazolidine at a high yield.

In accordance with the present invention, there is provided a production method of high purity 2-cyanoimino-1,3-thiazolidine at a high yield comprising cyclization reaction of dimethyl N-cyanoiminodithiocarbonate ester with 2-aminoethanethiol or the salt thereof in the presence of an alkali metal hydroxide.

MODE FOR CARRYING OUT THE INVENTION

The embodiments of the present invention will now be described in detail.

The reaction of the present invention is believed to proceed as in the following formulas:

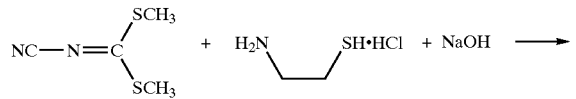

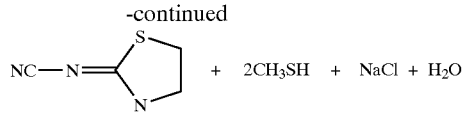

In a preferable embodiment of the production method of the present invention, an alkali metal hydroxide is first dissolved in water. The concentration of the alkali metal hydroxide is not particularly limited, but is preferably a low concentration from the viewpoint of agitation efficiency etc. since the dimethyl N-cyanoiminodithiocarbonate ester is insoluble in water and forms a slurry state. The specific concentration is 5 to 20% by weight, preferably 15 to 18% by weight of the total reaction mixture.

Specific examples of the alkali metal hydroxide used in the present invention are sodium hydroxide, potassium hydroxide, etc., but the use of sodium hydroxide is preferable from the viewpoints of economy and reactivity. These alkali metal hydroxides are used in amounts of preferably 0.01 to 0.25 mole, more preferably 0.04 to 0.12 mole, based upon 1 mole of 2-aminoethane thiol, and preferably 1.01 to 1.25 moles, more preferably 1.04 to 1.12 moles, based upon 1 mole of acid salt of 2-aminoethanethiol. If the amount of the alkali metal hydroxide is too small with respect to the 2-aminoethane thiol or the acid salt thereof, the improvement of the yield becomes harder to expect, while conversely if too large, the yield is liable to fall, and therefore, these are not preferred.

According to the present invention, 2-aminoethanethiol or the acid salt thereof (that is, an acid salt of 2-aminoethanethiol) is added to an aqueous solution of an alkali metal hydroxide, but 2-aminoethane thiol is easily oxidized in air and has poor storability. Further, since the solubility thereof in water is low, the use of an acid salt of 2-aminoethane thiol is preferred.

As the acid salt of 2-aminoethanethiol, a hydrochloride, sulfate, nitrate, carbonate, acetate, or the like alone or any combination thereof may be used, but the use of a mineral acid salt is preferable from the viewpoint of the reactivity, while a hydrochlorate is more preferable from the viewpoints of solubility, economy, etc. The 2-aminoethanethiol or the acid salt thereof is added to an aqueous solution of an alkali metal hydroxide preferably in such an amount that the molar ratio with the alkali metal hydroxide becomes in the above range, is dissolved, then the mixture is cooled to 0 to 5° C., preferably 0° C.

According to the present invention, at the time of reaction, the dimethyl N-cyanoiminodithiocarbonate ester is gradually added so that the temperature of the reaction mixture does not become 5° C. or more. After the completion of the addition of the dimethyl N-cyanoiminothiocarbonate ester, a cyclization reaction is preferably performed at 0° C. to 5° C.

The reaction ratio of the dimethyl N-cyanoiminothiocarbonate ester and 2-aminoethanethiol or the salt thereof is, by molar ratio, preferably 1:0.95 to 1.05, more preferably 1:0.99 to 1.01. If the amount of the 2-aminoethane thiol is too small, the yield is liable to be undesirably decreased, while conversely if too large, a polymerization reaction undesirably occurs more easily.

The reaction time of the cyclization reaction is not particularly limited, but, for example, is 10 minutes to 5 hours, preferably 1 to 3 hours. If the cyclization reaction time is too short, the cyclization reaction does not proceed sufficiently, while if too long, the reaction will not proceed further, and therefore this is not wise economically.

After the end of the reaction, the temperature of the reaction mixture was raised to 10 to 30° C., preferably to about 20° C., then the system was adjusted to a pH of 3 to 10 by a suitable acid, preferably 3 to 6. After the adjustment of the pH, an operation (aging) was performed to gradually raise the temperature in the system to about 40° C. and remove the byproduct, that is, methyl mercaptan, from the system. Note that, when removing the methyl mercaptan from the system, the rapid temperature rise becomes a cause of violent bubbling etc., and therefore, this is not preferred. Further, the temperature is not particularly limited, but after the operation for removing the methyl mercaptan from the system, the system is cooled to approximately room temperature, the operation of this procedure at a high temperature is not preferable in view of the process time. A temperature of about 35° C. to about 45° C. is preferable.

As specific examples of the acids used for controlling the pH of the reaction mixture, hydrochloric acid, sulfuric acid, nitric acid, carbonic acid, phosphoric acid, etc. may be mentioned, but from the economical viewpoints, the use of hydrochloric acid or sulfuric acid is preferred.

Also, the above-mentioned aging time is not particularly limited, but the treatment is preferably completed for preferably 1 to 5 hours, more preferably 2 to 3 hours. By removing the byproduct methyl mercaptan from the system in vacuo during the aging, it is possible to reduce the odor of the product and the surrounding environment.

According to the present invention, next, the resultant reaction mixture containing the 2-cyanoimino-1,3-thiazolidine obtained is again cooled to about 15° C. to about 25° C., preferably about 20° C., then the resultant 2-cyanoimino-1,3-thiazolidine is filtered and then washed. This washing can be performed with water or another solvent (for example, methanol, ethanol, etc.), but from the viewpoints of economy and environment, the washing with water is preferred.

The drying conditions of the 2-cyanoimino-1,3-thiazolidine thus produced are also not particularly limited and also differ depending on the type of the dryer, but when using a box type dryer, the drying is preferably carried out at a drying temperature of 60 to 120° C., more preferably 80 to 100° C., for a drying time of preferably 30 minutes to 24 hours, more preferably 3 to 6 hours, and a degree of vacuum of preferably 20 mmHg (i.e., 2,666 Pa) or less, more preferably 10 mmHg (i.e., 1,333 Pa) or less.

EXAMPLES

The present invention will now be described specifically using Examples, but the present invention is, of course, not limited to these Examples.

EXAMPLE 1

A 300 ml four-necked flask provided with a thermometer and an agitator was charged with 150 g of water (8.3 moles), then 11.2 g of 99% by weight sodium hydroxide (0.28 mole, 1.12 moles based upon 1 mole of 2-aminoethane thiol hydrochloride) was added while cooling and agitating to be dissolved in the water, then 28.8 g of 99.5% by weight 2-aminoethane thiol hydrochloride (0.25 mole) was added thereto and dissolved therein, then the reaction mixture was cooled to 0° C.

To this reaction mixture, 36.9 g of 99.5% by weight dimethyl N-cyanoiminodithiocarbonate ester (0.25 mole) was added so that the temperature inside the system became 5° C. or less. After the end of addition, the mixture was allowed to react at 0 to 5° C. for 2 hours.

Thereafter, the reaction mixture was heated to 20° C., adjusted in pH to 4.0 with 36% by weight aqueous hydrochloric acid solution, then further heated to 40° C. and allowed to age for 2 hours.

After aging, the reaction mixture was cooled to 20° C., then the crystals were suction filtered and washed with 100 g of water (5.6 moles) to obtain 36.6 g of 2-cyanoimino-1,3-thiazolidine.

The wet crystals were dried in vacuo at 80° C. under $6.7 \times 10^{-4}$ MPa for 5 hours to obtain 28.6 g of 99.7% purity 2-cyanoimino-1,3-thiazolidine (yield 89.8%=value converted to purity, based on the charged dimethyl N-cyanoiminodithiocarbonate ester). Note that the purity was analyzed by means of high pressure liquid chromatography (HPLC).

EXAMPLE 2

A 300 ml four-necked flask provided with a thermometer and an agitator was charged with 150 g of water (8.3 moles), then 12.3 g of 99% by weight sodium hydroxide (0.31 mole, 1.24 moles based upon 1 mole of 2-aminoethane thiol hydrochloride) was added, while cooling and agitating to be dissolved in the water, then 28.8 g of 99.5% by weight 2-aminoethane thiol hydrochloride (0.25 mole) was added thereto and dissolved therein. Thereafter, the reaction mixture was cooled to 0° C., then 36.9 g of 99.5% by weight dimethyl N-cyanoiminodithiocarbonate ester (0.25 mole) was gradually added so that the temperature inside the system became 5° C. or less. After the end of addition, the mixture was allowed to react for further 2 hours.

Next, the reaction mixture was heated to 20° C., adjusted in pH to 3.9 with 4.56 g (0.045 mole) of 36% by weight aqueous hydrochloric acid solution, then further heated to 40° C. and allowed to age for 2 hours.

After aging, the reaction mixture was cooled to 20° C., then suction filtered and washed with 200 g of water (11.1 moles) to obtain 34.7 g of wet crystals of 2-cyanoimino-1,3-thiazolidine.

The wet crystals obtained above, were dried in vacuo at 80° C. under $6.7 \times 10^{-4}$ MPa for 5 hours to obtain 27.9 g of 100% purity 2-cyanoimino-1,3-thiazolidine (yield 87.9%= value converted to purity, based on charged dimethyl N-cyanoiminodithiocarbonate ester).

Further, the total weight of the filtrate combined with the washings was 371.5 g. The filtrate included 0.98% of 2-cyanoiminothiazolidine (value converted to yield: 11.5%).

EXAMPLE 3

A 300 ml four-necked flask provided with a thermometer and an agitator was charged with 150 g of water (8.3 moles), then 10.6 g of 99% by weight sodium hydroxide (0.26 mole, 1.04 moles based upon 1 mole of 2-aminoethane thiol hydrochloride) was added, while cooling and agitating to be dissolved in the water, then 28.8 g of 99.5% by weight 2-aminoethane thiol hydrochloride (0.25 mole) was added thereto and dissolved therein. Thereafter, the reaction mixture was cooled to 0° C., then 36.9 g of 99.5% by weight dimethyl N-cyanoiminodithiocarbonate ester (0.25 mole) was gradually added so that the temperature inside the system became 5° C. or less, then was allowed to react for 2 hours.

Next, the reaction mixture was heated to 20° C., adjusted in pH to 9.2 with 0.25 g of 36% by weight aqueous hydrochloric acid solution (0.0025 mole), then further heated to 40° C. and allowed to age for 2 hours.

After aging, the reaction mixture was cooled to 20° C., then suction filtered and washed with 200 g of water (11.1 moles) to obtain 36.33 g of wet crystals of 2-cyanoimino-1,3-thiazolidine.

The wet crystals were dried in vacuo at 80° C. under $6.7 \times 10^{-4}$ MPa for 5 hours to obtain 27.2 g of 95.2% purity 2-cyanoimino-1,3-thiazolidine (yield 81.6%=value converted to purity, based on the charged dimethyl N-cyanoiminodithiocarbonate ester).

Further, the total weight of the filtrate combined with the washings was 361.5 g. The filtrate included 0.95% of 2-cyanoiminothiazolidine (value converted to yield: 10.8%).

COMPARATIVE EXAMPLE 1

A 300 ml four-necked flask provided with a thermometer and an agitator was charged with 100 g of water (5.6 moles), then 10.1 g of 99% by weight sodium hydroxide (0.25 mole) was added, while cooling and agitating to dissolve it. Next, 28.8 g of 99.5% by weight 2-aminoethane thiol hydrochloride (0.25 mole) was added thereto and dissolved therein, then 36.9 g of dimethyl N-cyanoiminodithiocarbonate ester (0.25 mole) was added and the mixture was heated and refluxed under agitation for 3 hours. After the end of the reaction, the reaction mixture was cooled to room temperature, then the crystals were suction filtered and washed with methanol and dried in vacuo at 80° C. under $6.7 \times 10^{-4}$ MPa for 5 hours to obtain 15.2 g of 99.7% purity 2-cyanoimino-1,3-thiazolidine (yield 47.7%= value converted to purity, based on the charged dimethyl N-cyanoiminodithiocarbonate ester).

REFERENCE EXAMPLE 1

To 500 ml of ethanol 146.24 g of dimethyl N-cyanoiminodithiocarbonate ester (1 mole) and 77.15 g of 2-aminoethane thiol (1 mole) were added. The mixture was heated and refluxed under agitation for 3 hours. After the end of the reaction, the mixture was cooled to room temperature, then the precipitated crystals were filtered. The crystals thus obtained were washed with ethanol, then dried to obtain 85.25 g of the above compound. (If making the purity of the above product 100%, the yield of the N-cyanoiminothiazolidine becomes 67.1%.)

COMPARATIVE EXAMPLE 2

A 300 ml four-necked flask provided with a thermometer and an agitator was charged with 114 g of water (6.3 moles), then 20.9 g of 99% by weight sodium hydroxide (0.50 mole) was added, while cooling and agitating, to be dissolved therein, then 28.8 g of 99.5% by weight 2-aminoethane thiol hydrochloride (0.25 mole) was added thereto and dissolved therein. Then, the reaction mixture was cooled to 0° C., then 36.9 g of 99.5% by weight dimethyl N-cyanoiminodithiocarbonate ester (0.25 mole) was gradually added, while holding the temperature to 5° C. or less, then the mixture was allowed to react for 2 hours.

Next, 30.9 g of 36% by weight aqueous hydrochloric acid solution (0.29 mole) was added to try to adjust the pH, but the mixture violently started bubbling at around pH 9.0 and finally the pH became 9.5. Next, the reaction mixture was suction filtered and washed with 200 g of water (11.1 moles) to obtain 28.6 g of wet crystals of 2-cyanoimino-1,3-thiazolidine.

The wet crystals were dried in vacuo at 80° C. under $6.7 \times 10^{-4}$ MPa for 5 hours to obtain 18.9 g of 100% purity 2-cyanoimino-1,3-thiazolidine (yield 59.4%=value converted to purity, based on the charged dimethyl N-cyanoiminodithiocarbonate ester).

COMPARATIVE EXAMPLE 3

A 300 ml four-necked flask provided with a thermometer and an agitator was charged with 150 g of water (8.3 moles), then 20.9 g of 99% by weight sodium hydroxide (0.50 mole) was added, while cooling and agitating, to be dissolved, then 28.8 g of 99.5% by weight 2-aminoethane thiol hydrochloride (0.25 mole) was added thereto and dissolved therein. Thereafter, the reaction mixture was cooled to 0° C., then 36.9 g of 99.5% by weight dimethyl N-cyanoiminodithiocarbonate ester (0.25 mole) was gradually added, while holding the temperature to 5° C. or less, the mixture was then allowed to react for 2 hours.

Next, 31.7 g of 36% by weight aqueous hydrochloric acid solution (0.31 mole) was added to try to adjust the pH, but the mixture violently started bubbling at around pH 9.0 and finally the pH became 1.7. Next, the reaction mixture was suction filtered and washed with 200 g of water (11.1 moles) to obtain 34.8 g of wet crystals of 2-cyanoimino-1,3-thiazolidine.

The wet crystals were dried in vacuo at B0° C. under $6.7 \times 10^{-4}$ MPa for 5 hours to obtain 20.7 g of 100% purity 2-cyanoimino-1,3-thiazolidine (yield 65.2%=value converted to purity, based on the charged dimethyl N-cyanoiminodithiocarbonate ester).

INDUSTRIAL APPLICABILITY

According to the method of the present invention, in the industrial scale production of 2-cyanoimino-1,3-thiazolidine, the various problems due to the prior art methods, in particular the problems of high cost and insufficient yield, can be solved and high purity 2-cyanoimino-1,3-thiazolidine can be produced at a high yield.

We claim:

1. A method for producing 2-cyanoimino-1,3-thiazolidine comprising cyclization reaction of dimethyl N-cyanoiminodithiocarbonate ester with 2-aminoethanethiol or the salt thereof in the presence of an alkali metal hydroxide.

2. A production method as claimed in claim 1, wherein a molar ratio of 2-aminoethane thiol and the alkali metal hydroxide is 1:0.01 to 0.25.

3. A production method as claimed in claim 1, wherein a molar ratio of the salt of 2-aminoethane thiol and the alkali metal hydroxide is 1:1.01 to 1.25.

4. A production method as claimed in claim 1, wherein said cyclization reaction is carried out in an aqueous solution.

5. A production method as claimed in claim 1, wherein byproducts are treated at a pH of 3 to 10 after said cyclization reaction.

6. A production method as claimed in claim 1, 2-aminoethanethiol is used as an acid salt.

7. A production method as claimed in claim 6, wherein the acid salt of 2-aminoethanethiol is at least one member of hydrochlorides, sulfates, nitrates, carbonates, and acetates.

* * * * *